United States Patent
Bolander et al.

(10) Patent No.: US 9,748,732 B2
(45) Date of Patent: Aug. 29, 2017

(54) SHEET LIGHT SOURCE USING LASER DIODE

(71) Applicant: Grote Industries, LLC, Madison, IN (US)

(72) Inventors: Albert Bolander, Jeffersonville, IN (US); Cesar Perez-Bolivar, Madison, IN (US); Michael Redwine, Madison, IN (US)

(73) Assignee: Grote Industries, LLC, Madison, IN (US)

( * ) Notice: Subject to any disclaimer, the term of this patent is extended or adjusted under 35 U.S.C. 154(b) by 0 days.

(21) Appl. No.: 15/150,526

(22) Filed: May 10, 2016

(65) Prior Publication Data
US 2016/0252220 A1    Sep. 1, 2016

Related U.S. Application Data

(63) Continuation of application No. 14/310,713, filed on Jun. 20, 2014, now Pat. No. 9,395,481.

(51) Int. Cl.
*F21V 5/00* (2015.01)
*H01S 5/022* (2006.01)
(Continued)

(52) U.S. Cl.
CPC .......... *H01S 5/0226* (2013.01); *A61N 5/0616* (2013.01); *B60Q 3/217* (2017.02);
(Continued)

(58) Field of Classification Search
CPC ................ F02B 6/0068; F02B 6/0083; A61N 2005/0643; A61N 2005/067;
(Continued)

(56) References Cited

U.S. PATENT DOCUMENTS

| 3,659,136 A | * | 4/1972 | Grodkiewicz | ....... C09K 11/777 252/301.4 H |
| 7,217,956 B2 | * | 5/2007 | Daniels | ..................... F21K 9/00 257/88 |

(Continued)

FOREIGN PATENT DOCUMENTS

EP    1669799 B1    6/2013

OTHER PUBLICATIONS

International Preliminary Report on Patentability mailed by the International Bureau of WIPO on Dec. 29, 2016, in connection with PCT international patent application No. PCT/US2015/031482, which corresponds to related U.S. Appl. No. 14/310,713.
(Continued)

*Primary Examiner* — Ali Alavi
(74) *Attorney, Agent, or Firm* — Posz Law Group, PLC

(57) ABSTRACT

A sheet light source is described that has a width in a front-to-back "x" direction, a length in a left-to-right "y" direction, and a height in a bottom-to-top "z" direction. The sheet light source includes a bottom conductive surface, a laser diode, a transparent conductive sheet, and an adhesive material portion. The laser diode is mounted on the conductive surface in the "z" direction. The transparent conductive sheet is laminated onto the laser diode and the conductive surface in the "z" direction. The adhesive material portion is located between the conductive sheet and the conductive surface, and binds the transparent conductive sheet to the laser diode and the conductive surface. The adhesive material portion further enables photons, emitted substantially in the "x" direction from the laser diode, to propagate therein to an edge and be output.

14 Claims, 5 Drawing Sheets

(51) Int. Cl.
*F21V 8/00* (2006.01)
*A61N 5/06* (2006.01)
*F21V 9/16* (2006.01)
*F21K 99/00* (2016.01)
*B60Q 3/64* (2017.01)
*B60Q 3/217* (2017.01)
*B60Q 3/78* (2017.01)
*F21W 131/20* (2006.01)
*F21W 101/08* (2006.01)
*A61N 5/067* (2006.01)
*F21Y 115/30* (2016.01)
*F21Y 101/02* (2006.01)
*F21Y 105/00* (2016.01)
*F21Y 115/10* (2016.01)

(52) U.S. Cl.
CPC ............... *B60Q 3/64* (2017.02); *B60Q 3/78* (2017.02); *F21K 9/56* (2013.01); *F21V 9/16* (2013.01); *G02B 6/0068* (2013.01); *G02B 6/0083* (2013.01); *A61N 2005/067* (2013.01); *A61N 2005/0645* (2013.01); *A61N 2005/0651* (2013.01); *A61N 2005/0652* (2013.01); *A61N 2005/0659* (2013.01); *A61N 2005/0663* (2013.01); *F21W 2101/08* (2013.01); *F21W 2131/20* (2013.01); *F21Y 2101/025* (2013.01); *F21Y 2105/00* (2013.01); *F21Y 2115/10* (2016.08); *F21Y 2115/30* (2016.08)

(58) Field of Classification Search
CPC ....... A61N 2005/0663; F21W 2101/08; F21W 2101/20; F21Y 2101/025
See application file for complete search history.

(56) References Cited

U.S. PATENT DOCUMENTS

| | | | |
|---|---|---|---|
| 7,374,315 B2 | 5/2008 | Dorsey et al. | |
| 8,487,518 B2 | 7/2013 | Johnston et al. | |
| 9,395,481 B2* | 7/2016 | Bolander | B60Q 3/0289 |
| 2007/0121129 A1* | 5/2007 | Eida | B82Y 20/00 |
| | | | 358/1.9 |
| 2007/0194332 A1 | 8/2007 | Daniels et al. | |
| 2008/0079012 A1 | 4/2008 | Grote et al. | |
| 2009/0056995 A1* | 3/2009 | Maeda | B32B 15/08 |
| | | | 174/259 |
| 2010/0246166 A1 | 9/2010 | Hsu et al. | |
| 2012/0163020 A1* | 6/2012 | Inada | G02B 6/006 |
| | | | 362/606 |
| 2013/0027955 A1* | 1/2013 | Grote, III | F21K 9/00 |
| | | | 362/510 |

OTHER PUBLICATIONS

International Search Report and Written Opinion of the International Searching Authority mailed Oct. 8, 2015 in connection with PCT international patent application No. PCT/US2015/031482 which corresponds to related U.S. Appl. No. 14/310,713.

* cited by examiner

SHEET LIGHT SOURCE USING LASER DIODE

CROSS REFERENCE TO RELATED APPLICATION

This application is a continuation of U.S. patent application Ser. No. 14/310,713 (now U.S. Pat. No. 9,395,481), filed Jun. 20, 2014, the disclosure of which is incorporated herein by reference.

TECHNICAL FIELD

The technical field relates in general to a laser diode lighting device. More specifically, the technical field relates to a sheet light source formed with one or more electrically connected laser diodes.

BACKGROUND

Edge illumination is necessary for a variety of different parts in a vehicle, such as in cup holders and in door illumination. Edge illumination can be achieved using a light active sheet that is described in more detail in U.S. Pat. No. 7,217,956 and in U.S. Patent Application Publication No. 2008/0079012, both of which are fully incorporated herein by reference. The light active sheet described in these documents is referred to in this disclosure simply as "light sheet" or "light sheet technology."

FIG. 5 is a cross-section of related light sheet technology 501. In FIG. 5, the following x-y-z directions are utilized for ease of describing relationships of components. A light sheet can generally have a width from edge-to-edge (or a front-to-back direction) along direction x, a length from left side to right side (or a left-to-right direction) along direction y, and a top-bottom direction along direction z.

The light sheet 501 may include a first substrate 503, a second substrate 507, an adhesive layer 505 sandwiched between the first and second substrates, and a light emitting diode (LED) 517 that is embedded in the adhesive 505. First and second indium tin oxide (ITO) layers 509, 511 are sandwiched between the respective first and second substrates 503, 507 and the adhesive layer 505.

The first and second substrates 503, 507 may be transparent or clear substrates. The first and second substrates 503, 507 may be polyethylene naphthalate (PEN), polyethylene terephthalate (PET), and/or polycarbonate. The first and second ITO layers 509, 511 can be provided as a coating on the respective first and second substrates 503, 507. The first and second substrates 503, 507 in combination with the first and second ITO layers 509, 511 form top and bottom electrically conductive transparent substrates. The adhesive layer can be a non-conductive transparent adhesive material.

The LED 517 can be one of plural LEDs. The LED 517 has a top surface which is perpendicular to a planar surface of the first substrate 503. When powered, the LED 517 emits photons 521 principally from the top surface (sometimes referred to as a "light emitting surface"). Because the top surface of the LED 517 is perpendicular to a planar surface of the first substrate 503, the light photons 521 are emitted generally up and through the first substrate 503 from the LED 517. The LED 517 is illustrated with photons being emitted.

Also illustrated in FIG. 5 is a first positive (+) copper bus 513 and second negative (−) copper bus 515 which power the ITO layers 509, 511 and thus power the LED 517. The LED 517 is representative of plural LEDs disposed along a left-to-right (y) direction. The layered structure of the light sheet typically is extended along a front-to-back direction to include plural LEDs. The basic structure of this light active sheet material is disclosed in more detail in U.S. Pat. No. 7,217,956 referenced above.

The above described light sheet is quite useful and efficient in producing light when viewed from above in the z direction. However, such a light sheet requires relatively larger amounts of space for placement. Therefore, the light sheet described above would not be particularly useful in edge lighting.

In order to modify the light sheet described above for edge lighting, the photons must be emitted in some manner in a front-to-back direction which is indicated as being in the x direction in FIG. 5. One approach to forcing the photons to move in the x direction is seen in U.S. Patent Application Publication Nos. 2013/0026504 and 2013/0027955, which are also expressly incorporated herein by reference. In these documents, the disclosed approach to redirecting photons is to provide additional layers of film that reflect the photons in the desired direction. However, adding film layers to the light sheet expands the size of the sheet as well as the costs of production of the light sheet.

The embodiments disclosed herein offer a simpler, less costly, and much more efficient approach to emitting photons in a front-to-back direction from a light sheet configured in a bottom-to-top direction. Specifically, one or more laser diodes are used which produce a highly concentrated photon emission in a front-to-back (x) direction. The use of a laser diode in a light sheet can produce a luminous intensity that is greater than the luminous intensity provided by the solutions described in the applications mentioned above by a factor of 1,000.

SUMMARY

Accordingly, an embodiment disclosed herein provides a sheet light source. The sheet light source has a width in a front-to-back "x" direction, a length in a left-to-right "y" direction, and a height in a bottom-to-top "z" direction. The sheet light source includes a bottom conductive surface, at least one laser diode, a transparent conductive sheet, and an adhesive material portion.

The at least one laser diode is mounted on the bottom conductive surface in the "z" direction. The transparent conductive sheet is laminated onto the at least one laser diode and the conductive surface in the "z" direction. The adhesive material portion is disposed between the transparent conductive sheet and the bottom conductive surface. The adhesive material portion binds the transparent conductive sheet to the laser diode and the conductive surface, and allows photons, emitted substantially in the "x" direction from the at least one laser diode, to propagate therein to an edge and be output. Second and third embodiments disclosed herein provide an edge lighting device and bandage device, each utilizing a sheet light source as described above, except including a plurality of laser diodes.

It should be noted that the purpose of the foregoing Abstract is to enable the U.S. Patent and Trademark Office and the public generally, and especially the scientists, engineers and practitioners in the art who are not familiar with patent or legal terms or phraseology, to determine quickly the nature and essence of the technical disclosure of the application. The Abstract is neither intended to define the invention of the application, which is measured by the claims, nor is it intended to be limiting as to the scope of the invention in any way.

BRIEF DESCRIPTION OF THE DRAWINGS

The accompanying figures, where like reference numerals refer to identical or functionally similar elements, and which together with the detailed description below are incorporated in and form part of the specification, serve to further illustrate various exemplary embodiments and to explain various principles and advantages in accordance with the embodiments.

DETAILED DESCRIPTION

In overview, the present disclosure concerns light sheet technology that makes use of a laser diode for light emission that is substantially perpendicular to the components of the light sheet as stacked from top to bottom. Such perpendicular light emission is particularly useful in edge lighting where a plurality of laser diodes is electrically connected in the light sheet. The instant disclosure is thus provided to further explain in an enabling fashion one or more embodiments of an inventive light source using a laser diode in light sheet technology.

This disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is further understood that the use of relational terms such as first and second, and the like, if any, are used solely to distinguish one from another entity, item, or action without necessarily requiring or implying any actual such relationship or order between such entities, items or actions. It is noted that some embodiments may include a plurality of processes or steps, which can be performed in any order, unless expressly and necessarily limited to a particular order; i.e., processes or steps that are not so limited may be performed in any order.

Figure 1:
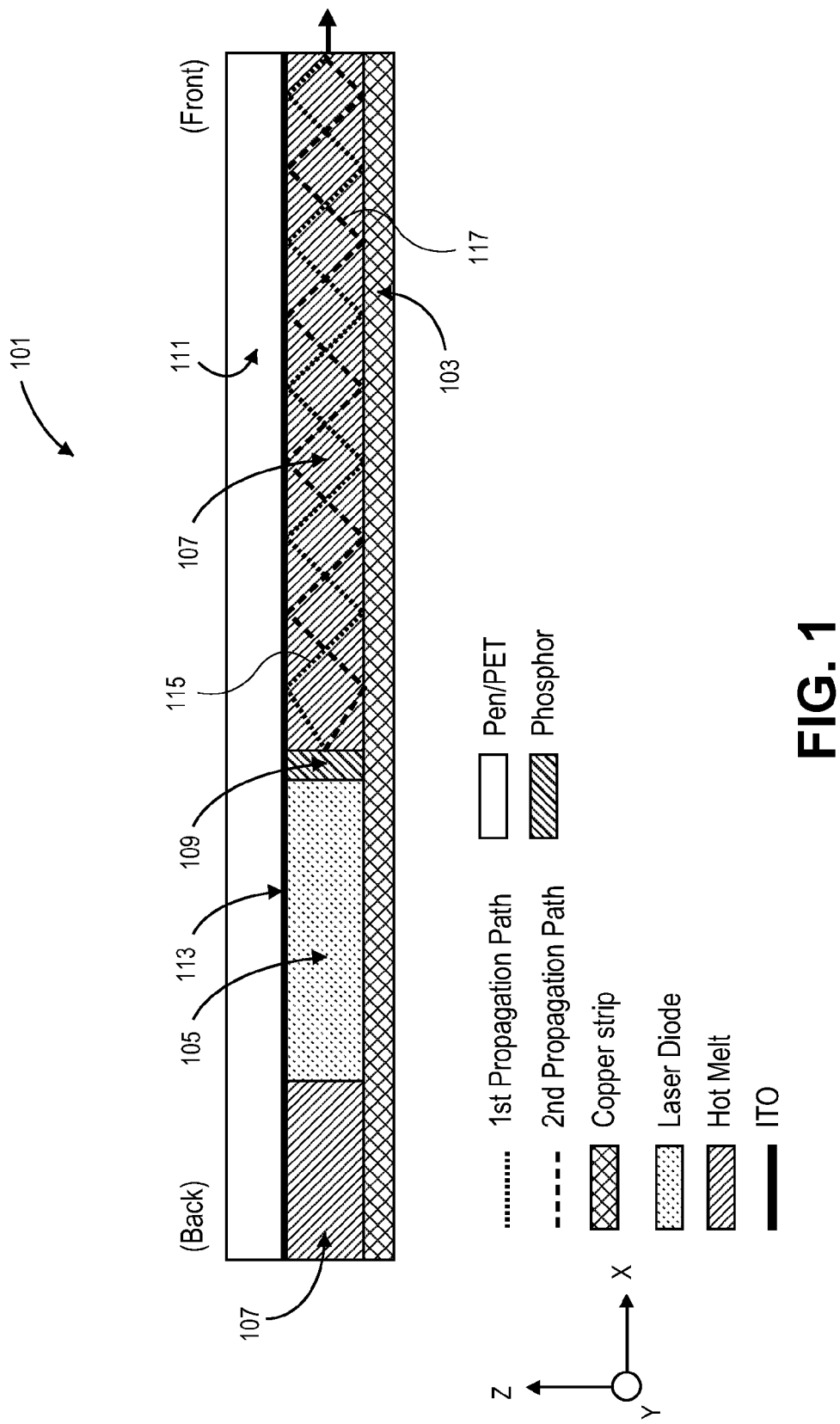
FIG. 1 is a cross-section of a light sheet using a laser diode light source.
Figure 5:
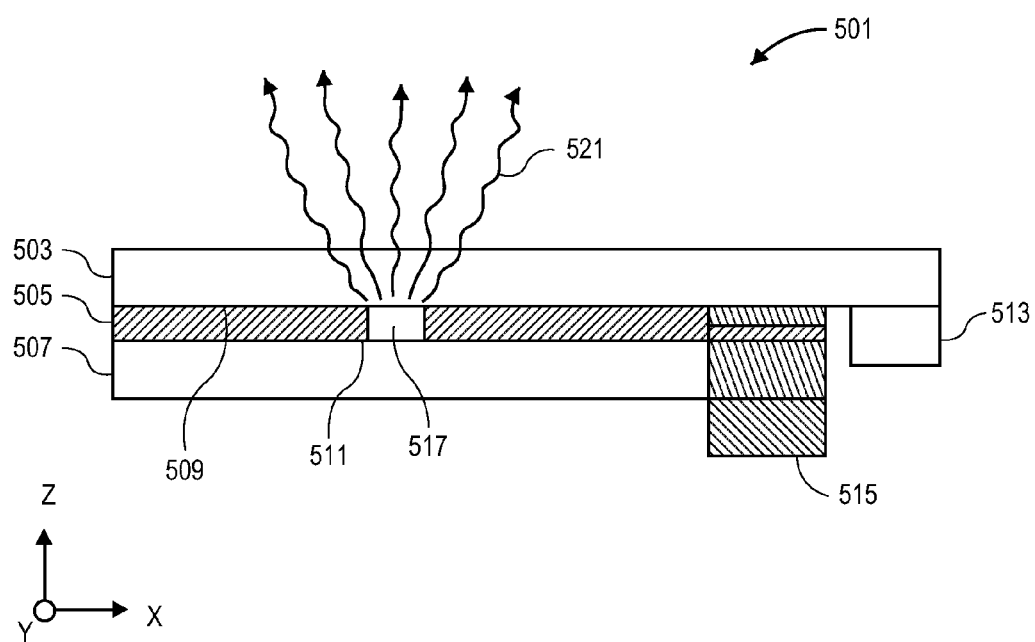
FIG. 5 is a cross-section of related light sheet technology.

Referring now to FIG. 1, a cross-section of a light sheet 101 using a laser diode light source 105 is discussed and described. The light sheet 101 comprises a metal substrate 103, the laser diode 105, an adhesive 107, a conversion layer 109, a substrate 111, and a conductive sheet layer 113. Like FIG. 5, the light sheet 101 should be viewed on a three-dimensional scale where a width from front-to-back is given by an "x" direction, a length from left-to-right (for example, when viewed from the right end of the page) is given by a "y" direction, and a height from bottom-to-top is given by a "z" direction.

The bottom metal substrate 103 provides a firm and solid contact with a voltage source. The metal substrate 103 may be formed of any well-known conductive metal that typically would be inexpensive in the manufacturing process, such as copper. Copper in particular is known for its conductive properties as well as its relatively inexpensive costs. However, the metal substrate 103 can also be formed from other conductive metals such as gold, platinum, aluminum or silver, and alloys such as brass, bronze, palladium silver or aluminum alloys. The bottom metal substrate 103 functions as a cathode in operation of the laser diode 105.

In light sheet technology, the substrate 111 may typically be a polyethylene naphthalate (PEN) substrate, a polyethylene terephthalate (PET) substrate, a polyimide (PEEK) substrate, or a transparent conductive polyester substrate. These substrates are chosen because they can be manufactured in a continuous strip, are flexible, and are compatible with roll to roll manufacturing. These properties of the substrate 111 allow a plurality of laser diodes to be disposed in the same manner as seen in FIG. 1, but spaced apart in the y direction. The substrates can be rolled such that the light sheets can be placed in hard-to-get-to areas that are required for edge lighting.

The conductive sheet layer 113 disposed below the substrate 111 is a transparent conductive sheet such that when a plurality of laser diodes are disposed in the same manner as seen in FIG. 1, but spaced apart in the y direction, the plurality of laser diodes will maintain electrical connectivity. The conductive sheet layer 113 may be formed of indium tin oxide (ITO). Other transparent conductive oxides may also be used. Another possible substance to coat onto the top substrate 111 is carbon nanotubes. These are just examples, and one of ordinary skill in the art would understand that any electrically conductive, optically clear material can be used to electrically connect a plurality of laser diodes. It should be noted that the conductive sheet layer 113 operates as an anode in operating the laser diode 105.

The top substrate 111 is formed on an adhesive layer 107. The adhesive layer 107 exists substantially in all areas between the top substrate 111 and the metal substrate 103 not otherwise occupied by a laser diode 105. As indicated by the name, the adhesive layer 107 serves to adhere the metal substrate 103, the top substrate 111, and any laser diodes 105 that are electrically connected by the conductive sheet 113. An appropriate material for use as the adhesive layer 107 is a hot melt adhesive, for example an EVA (ethylene vinyl acetate) adhesive, a polyurethane adhesive, a polyolefin adhesive, a polyamide adhesive, or similar material. As described further below, photons emitted from the laser diode 105 move through the adhesive 107 to an edge of the adhesive where they are output as visible light.

Turning now to the laser diode 105 itself, it should be understood that there are a plurality of commercially available laser diodes on the market that can be used within the light sheet 101. The primary characteristic of the laser diode 105, when used in the light sheet 101 is that photons are emitted from the laser diode 5 in the x direction when the diode is electrically connected in the z direction between the conductive metal 103 and the conductive sheet 113.

Figure 2:
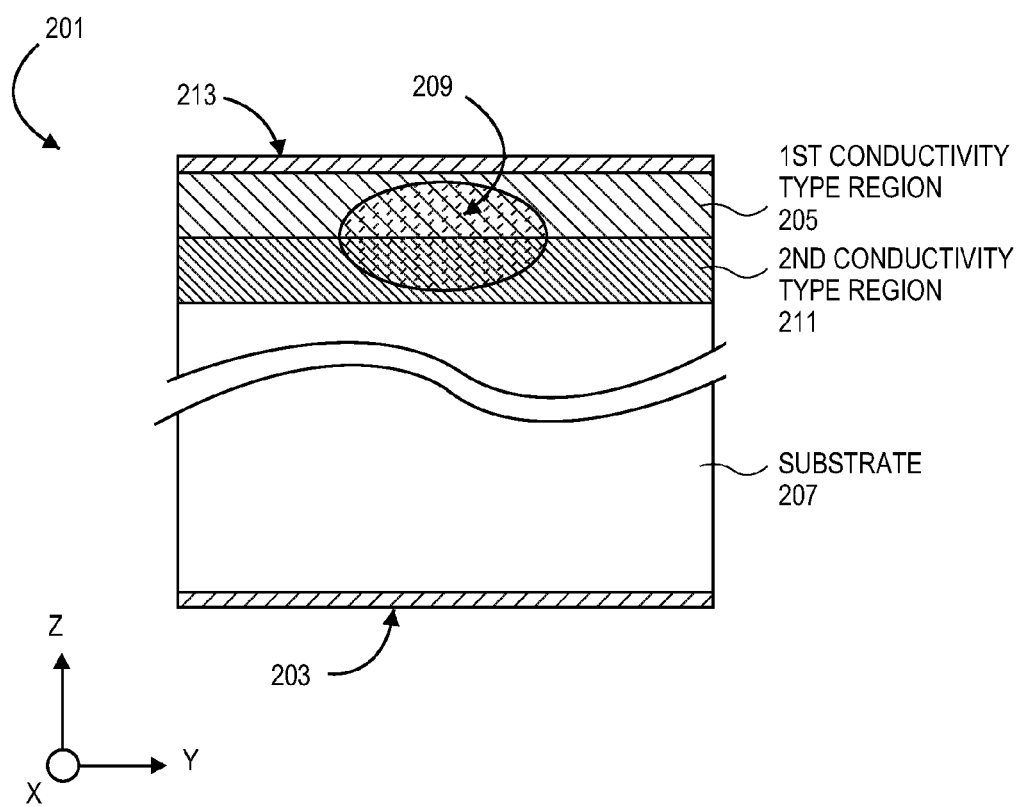
FIG. 2 is a cross-section of a simple laser diode for use in a light sheet.

This perpendicular emission of photons from the mounting direction of the laser diode 105 is in fact a property that is inherent and well-known with respect to commercially available laser diodes. FIG. 2, which is a cross-section of a simple laser diode 201 for use in a light sheet 101, is now discussed and described. The laser diode 201 comprises a $1^{st}$ conductivity type region 205, a $2^{nd}$ conductivity type region 211, and a substrate 207. The material that forms the $2^{nd}$ conductivity type region 211 may be the same as the material that forms the substrate 207 but with a difference in concentration of dopants.

The laser diode 201 is connected between a first metal contact 203 and a second metal contact 213 that powers the laser diode 201. In practice, the laser diode 201 may be integrated into the light sheet 101 such that the conductive metal 103 in FIG. 1 serves as the bottom metal contact 203 of FIG. 2, and the conductive sheet layer 113 serves as top metal contact 213. Alternatively, the laser diode 201 may be fabricated with the metal contacts 203 and 213, and are further placed between the conductive metal 103 and the conductive sheet layer 113 of FIG. 1. Conductivity would be ensured under either condition.

As can be seen in FIG. 2, the combination of carriers in the laser diode produce a beam of photons extending in the x direction out of the page, which is in accord with the x direction in FIG. 1. That is to say, photons are emitted from the laser diode 201 in a direction substantially equivalent to the back-to-front direction x seen in FIG. 1. Thus as seen in FIG. 1, photons are emitted into the hot melt 107, and are refracted along various trajectories 115, 117 within the hot melt 107 until they reach the edge of the light sheet 101 where they are output as visible light.

It should be noted that the conductivity type regions 205, 211 of illustrated laser diode 201 can alternate between P type conductivity regions and N type conductivity regions. That is to say, a more traditional configuration of laser diode has a P type conductivity region as top-most, $1^{st}$ conductivity type region 205 abutting the metal contact 213, and an N type conductivity region forming the lower, $2^{nd}$ conductivity type region 211.

An alternative configuration of a laser diode has an a N type conductivity region as top-most, $1^{st}$ conductivity type region 205 abutting the metal contact 213, and a P type conductivity region forming the lower, $2^{nd}$ conductivity type region 211. This configuration of the laser diode 201 is sometimes referred to as an "N up" configuration due to the fact that the N type region is upward of the P type region.

The laser diode 201 of FIG. 2 is very much a simplified version of an actual laser diode that may be used in a light sheet 101 in actual practice. The diode 201 is illustrated with two conductivity type regions 205, 211 to simply demonstrate the emission of light from the isolation regions 209. However, in practice the configuration of the laser diode is more complex. It should be understood that this disclosure contemplates the use of laser diodes currently known in the art as well as those yet to be developed. Examples of well-known laser diodes include double heterostructure lasers, quantum well lasers, quantum cascade lasers, separate confinement heterostructure lasers, distributed feedback lasers, vertical-cavity surface-emitting lasers (VCSELs), vertical-external-cavity surface-emitting-laser (VECSELs), and external-cavity diode lasers.

Returning now to FIG. 1, it should be noted that the light sheet 101 includes a dedicated conversion layer 109. The conversion layer 109 either up-converts or down-converts the wavelength of the photons emitted from the laser diode 105 in order to change the color of the light emitted from the laser diode 105. Conversion of light is well known when using conventional light emitting diodes (LEDs) which often times are designed to strongly emit high energy, short wavelength blue light.

When using conventional LEDs, various materials, including phosphor, may be used to down-convert the blue light into any longer wavelength light such as a green, yellow, orange, or red light. This same type of down-conversion can be used in a light sheet 101 with a laser diode 105 by simply forming the conversion layer 109 out of the necessary material.

Although down-conversion of light remains available in a light sheet 101, the use of the laser diode 105 also offers the option of up-conversion of light. More particularly, up-conversion of light is a much more inefficient operation than down-conversion of light, as is known in the art. Because of the much higher light yield using the laser diode 105, up-conversion of light can be reliably performed. Thus in a light sheet 101, the chosen laser diode 105 may naturally emit a higher wavelength light such as red light, yellow light, and even infrared light. Using a conversion layer 109 made of phosphor, light emitted from the laser diode 105 that is of either red light, yellow light, or infrared light may be up-converted to either green light or blue light.

The use of a conversion layer 109 allows for production of light sheets 101 using laser diodes 105 of different types without particular attention to the color of the light produced. This of course has certain production advantages. At this point, it should be noted that the inclusion of the conversion layer 109 in the configuration of the light sheet 101 is primarily for demonstrating how down-conversion or up-conversion occurs. While a dedicated conversion layer 109 can certainly be used for conversion of light, in practice it may be more efficient to simply incorporate the conversion material into the adhesion layer 107 (that is, the hot melt layer).

For example, phosphor particles can be included in the hot melt 107. When photons are emitted directly into the hot melt 107, the phosphor in the hot melt 107 will cause the up-conversion to occur. The wavelength of emitted light from the diode 105 will thus change in the hot melt 107 itself.

It should be noted that in FIG. 1, photons are seen taking either a $1^{st}$ propagation path 115 or a $2^{nd}$ propagation path 117. These two emissions paths 115, 117 are included to simply demonstrate that photons are refracted in the adhesive/hot melt layer 107 as they travel to the edge of the light sheet 101. The propagation paths 115, 117 do not indicate that photons may be of different wavelengths, and that the photons may or may not have been converted. Nonetheless, FIG. 1 demonstrates that all photons emitted from the laser diode 105 will embark on some propagation path that eventually leads to an edge of the light sheet 101 where the photons are output. At this point, the light becomes visible to humans.

As mentioned above, a plurality of laser diodes, spaced apart in the y direction, can be electrically connected by the conductive metal 103 and the conductive sheet layer 113. When viewed from the edge of the light sheet 101 in the x direction, the plurality of laser diodes will illuminate what appears to be an edge. Thus a light sheet in accord with FIG. 1 can be used for edge lighting.

Figure 3:
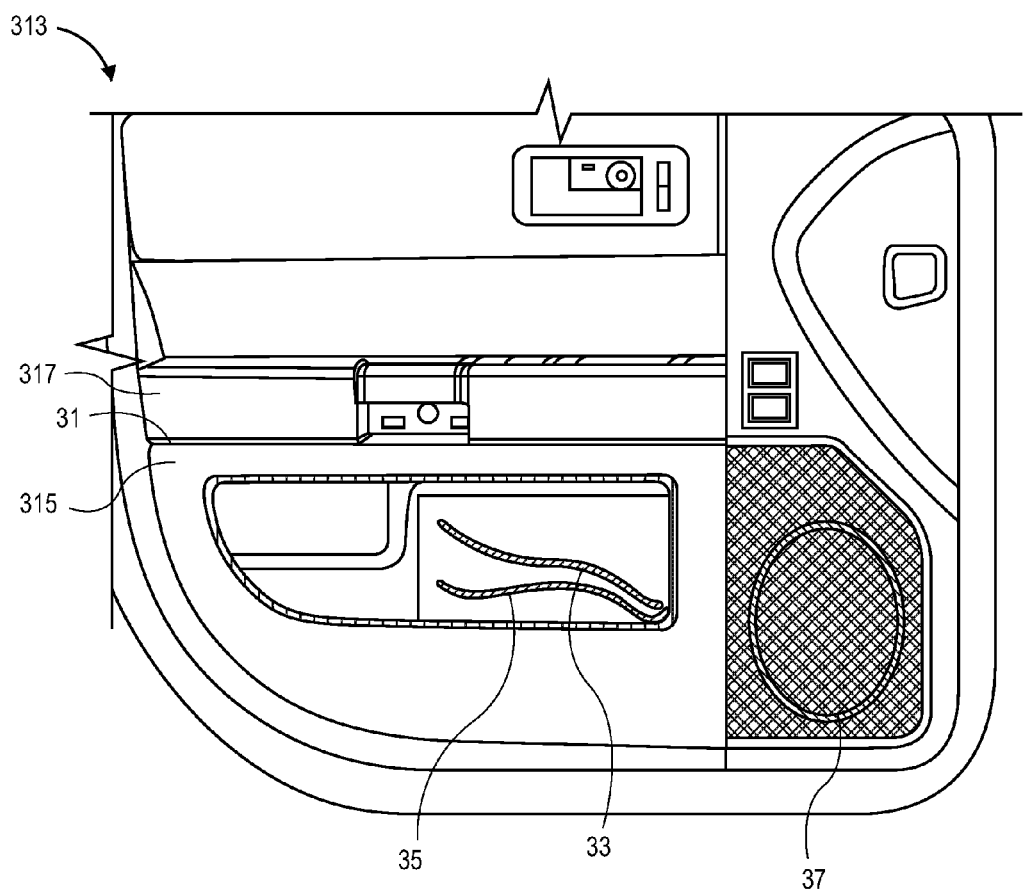
FIG. 3 is a view of a plurality of light sheets, each using a plurality of laser diodes, forming edge lighting in a vehicle door.

FIG. 3 is a view of such edge lighting. More specifically, FIG. 3 shows a plurality of light sheets, each using a plurality of laser diodes, which form edge lighting in a vehicle door 313. Specifically, the vehicle door 313 is provided with edge lighting 31, 33, 35, 37. As discussed above, the light is emitted in and refracts within an adhesive hot melt within the light sheet, and is directed to the edge of the light sheet. A thin ribbon of light from the edge of the light sheet is thereby presented.

A lighting device in the form a light sheet can be thin, for example less than 0.02 inches in thickness. This enables light to be installed in areas often times unrealized. The light sheets can be installed in pre-determined gaps that conventionally exist, thus avoiding additional tooling costs.

As an example, edge lighting 31 in the form of a light sheet can be placed within the designed gap between first and second door trim pieces 315, 317 wherein the light sheet 31 is sandwiched between the door trim pieces 315, 317. The edge of the light sheet from which light is output is of course exposed. The gap in the door is created according to normal specifications for first and second door trim pieces 135, 317. The edge lighting 31 simply fills what would otherwise be an empty gap.

Edge lighting 33, 35 from light sheets can be sandwiched in gaps within trim pieces such as the illustrated door pocket. Edge lighting 37 from a light sheet can be formed in a pocket around a stereo speaker. Edge lighting can be used in other, even more difficult gaps such as in "cup holders" (not shown).

Edge lighting is flexible, and can be installed around corners with a radius as low as 1 inch. Edge lighting provides a uniform light, and will not dim around corners. Succinctly put, edge lighting, taking the form of the herein disclosed light sheets, provides several unique advantages.

Figure 4:
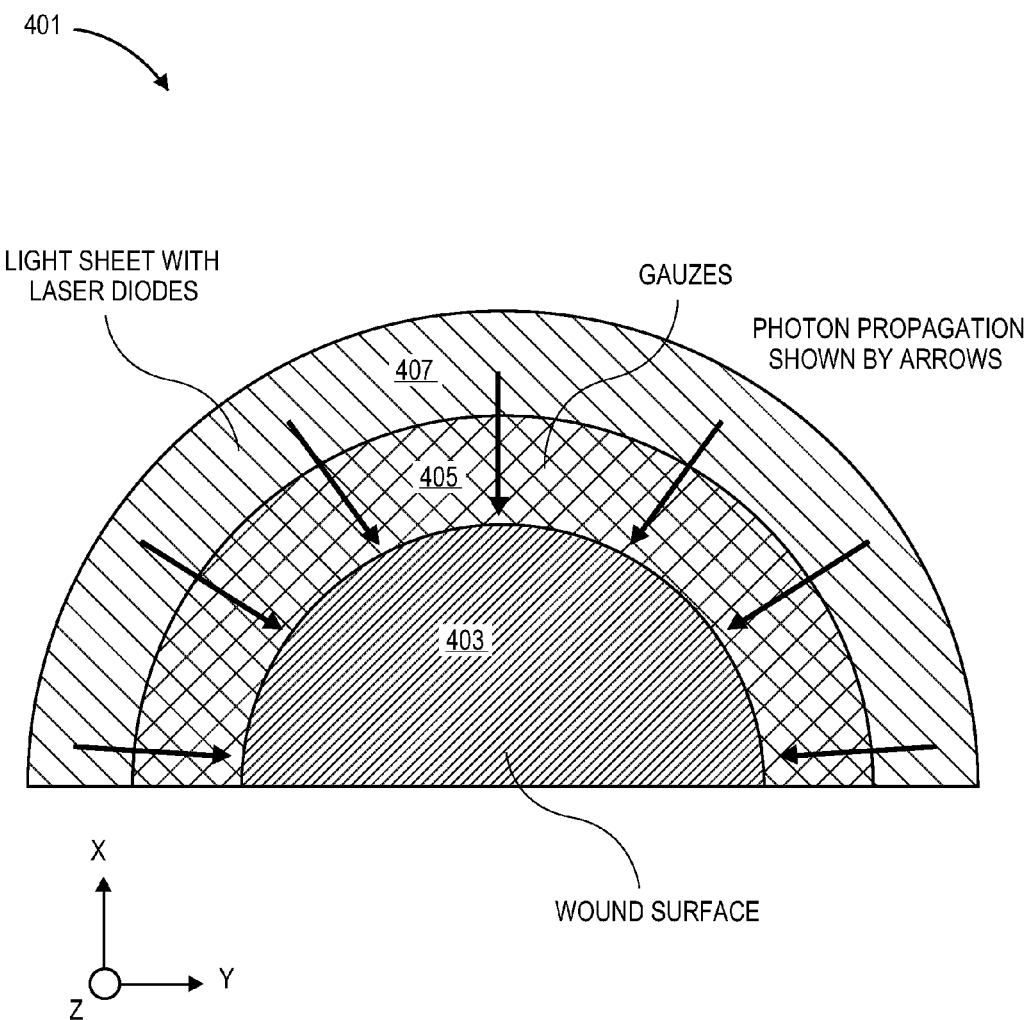
FIG. 4 is a cross-section diagram of a bandage device, using a light sheet with a plurality of laser diodes, irradiating a wound.

Although light sheets technology using laser diodes is certainly useful in providing edge illumination, there are other applications for this technology. Referring now to FIG. 4, a cross-section diagram of a bandage device 401, using a light sheet 407 with a plurality of laser diodes, irradiating a wound 403, is discussed and described. The use of the bandage device 401 is considered because the medical literature reflects that various wounds, and even subcutaneous conditions, may be treated in part by an accelerated bombardment of light.

The bandage device 401 is seen from what might be referred to as a plan view. That is to say, the components of the light sheet 407 are stacked on top of each other either into, or out from, the page. The axis of FIG. 4 therefore shows that the z-axis extends into the page. One can imagine that if the light sheet 407 were extended into a straight line from its curved position (that is the bottom left and right portions were extended upward), the view of the light sheet 407 would be from above looking at the top PEN/PET substrate (or possibly the bottom copper substrate, depending on the power arrangement).

FIG. 4 may also be described as looking, for example, at a finger from the end of the finger toward the hand. The bandage device 401 at least would partially surround the finger. As photons are emitted substantially perpendicular to the z direction in which a laser diode is mounted between a bottom conductive surface and a top transparent conductive sheet, the bandage device 401 is characterized by emission of photons from the light sheet 407 through gauzes 405, and into the wound 403. The propagation of photons is shown in FIG. 4 by the large arrows. The gauzes 405 are of course provided for comfort.

This disclosure is intended to explain how to fashion and use various embodiments in accordance with the invention rather than to limit the true, intended, and fair scope and spirit thereof. The invention is defined solely by the appended claims, as they may be amended during the pendency of this application for patent, and all equivalents thereof. The foregoing description is not intended to be exhaustive or to limit the invention to the precise form disclosed. Modifications or variations are possible in light of the above teachings. The embodiment(s) was chosen and described to provide the best illustration of the principles of the invention and its practical application, and to enable one of ordinary skill in the art to utilize the invention in various embodiments and with various modifications as are suited to the particular use contemplated. All such modifications and variations are within the scope of the invention as determined by the appended claims, as may be amended during the pendency of this application for patent, and all equivalents thereof, when interpreted in accordance with the breadth to which they are fairly, legally, and equitably entitled.

What is claimed is:

1. A sheet light source having a width in a front-to-back "x" direction, a length in a left-to-right "y" direction, and a height in a bottom-to-top "z" direction, comprising:
   a bottom metal substrate;
   at least one laser diode mounted on the metal substrate in the "z" direction;
   a transparent conductive sheet, with carbon nanotubes coated thereon, laminated onto the at least one laser diode and the bottom metal substrate in the "z" direction; and
   a hot melt adhesive material, disposed substantially in all areas between the transparent conductive sheet and the bottom metal substrate not otherwise occupied by the at least one laser diode,
      that binds the transparent conductive sheet to the at least one laser diode and the bottom metal substrate, and
      that enables photons, emitted substantially in the "x" direction from the at least one laser diode, to propagate therein to an edge and be output.

2. The sheet light source according to claim 1, wherein:
   the at least one laser diode includes a plurality of laser diodes mounted on the bottom metal substrate in the "z" direction, spaced apart in the "y" direction, and connected to each other by the transparent conductive sheet, and
   photons, emitted from each of the plurality of laser diodes in the "x" direction, propagate through the hot melt adhesive material to an edge of the hot melt adhesive material where the photons, emitted from each of the plurality of laser diodes, are output.

3. The sheet light source according to claim 2, wherein:
   each of the plurality of laser diodes is contacted by a respective phosphor layer disposed in the "x" direction from a respective laser diode and contacting a side in the "z" direction of the respective laser diode, and
   the photons, emitted from each of the plurality of laser diodes, which are of a first wavelength, are upconverted by the respective phosphor layer to a second, shorter wavelength.

4. The sheet light source according to claim 3, wherein at the first wavelength, the photons are infrared, and at the second, shorter wavelength, the photons produce a blue color.

5. The sheet light source according to claim 2, wherein the hot melt adhesive material includes a phosphor dispersed therein such that photons, emitted from each of the plurality of laser diodes, which are of a first wavelength, are upconverted by the phosphor to a second, shorter wavelength.

6. The sheet light source according to claim 5, wherein at the first wavelength, the photons are infrared, and at the second, shorter wavelength, the photons produce a blue color.

7. The sheet light source according to claim 2, wherein the bottom conductive surface is one of copper, gold, platinum, aluminum, silver, brass, bronze, palladium silver, and any aluminum alloy.

8. The sheet light source according to claim 2, wherein the hot melt adhesive material is one of an ethylene vinyl acetate (EVA) adhesive, a polyurethane adhesive, a polyolefin adhesive, and a polyamide adhesive.

9. The sheet light source according to claim 1, further comprising:

a phosphor layer, disposed in the "x" direction from the at least one laser diode and contacting a side in the "z" direction of the at least one laser diode, wherein the photons, emitted from the at least one laser diode, which are of a first wavelength, are upconverted by the phosphor layer to a second, shorter wavelength.

10. The sheet light source according to claim 9, wherein at the first wavelength, the photons are infrared, and at the second, shorter wavelength, the photons produce a blue color.

11. The sheet light source according to claim 1, wherein the hot melt adhesive material includes a phosphor dispersed therein such that photons, emitted from the at least one laser diode, which are of a first wavelength, are upconverted by the phosphor to a second, shorter wavelength.

12. The sheet light source according to claim 11, wherein at the first wavelength, the photons are infrared, and at the second, shorter wavelength, the photons produce a blue color.

13. The sheet light source according to claim 1, wherein the bottom conductive surface is one of copper, gold, platinum, aluminum, silver, brass, bronze, palladium silver, and any aluminum alloy.

14. The sheet light source according to claim 1, wherein the hot melt adhesive material is one of an ethylene vinyl acetate (EVA) adhesive, a polyurethane adhesive, a polyolefin adhesive, and a polyamide adhesive.

* * * * *